United States Patent
Kumar

(10) Patent No.: US 9,171,696 B2
(45) Date of Patent: Oct. 27, 2015

(54) ORIENTATION IMAGING USING WIDE ANGLE CONVERGENT BEAM DIFFRACTION IN TRANSMISSION ELECTRON MICROSCOPY

(71) Applicant: Vineet Kumar, Latrobe, PA (US)

(72) Inventor: Vineet Kumar, Latrobe, PA (US)

(*) Notice: Subject to any disclaimer, the term of this patent is extended or adjusted under 35 U.S.C. 154(b) by 0 days.

(21) Appl. No.: 14/298,249

(22) Filed: Jun. 6, 2014

(65) Prior Publication Data

US 2014/0346351 A1  Nov. 27, 2014

Related U.S. Application Data

(63) Continuation of application No. 13/192,443, filed on Jul. 27, 2011, now Pat. No. 8,748,817.

(60) Provisional application No. 61/368,154, filed on Jul. 27, 2010.

(51) Int. Cl.

| | | |
|---|---|---|
| *G01N 23/20* | (2006.01) | |
| *G01N 23/225* | (2006.01) | |
| *H01J 37/22* | (2006.01) | |
| *G01N 23/203* | (2006.01) | |
| *G01N 33/38* | (2006.01) | |
| *H01J 37/28* | (2006.01) | |

(52) U.S. Cl.
CPC .............. *H01J 37/22* (2013.01); *G01N 23/203* (2013.01); *G01N 33/385* (2013.01); *H01J 37/28* (2013.01); *H01J 2237/24571* (2013.01); *H01J 2237/2802* (2013.01)

(58) Field of Classification Search
CPC ............ H01J 2237/2802; H01J 37/222; H01J 37/295; G01N 23/20; G01N 23/2055
See application file for complete search history.

(56) References Cited

U.S. PATENT DOCUMENTS

| | | | | |
|---|---|---|---|---|
| 4,553,030 A | * | 11/1985 | Tokiwai et al. ................ | 250/311 |
| 4,626,689 A | * | 12/1986 | Tomita et al. ...................... | 850/9 |
| 2003/0012334 A1 | * | 1/2003 | Kurtz et al. ...................... | 378/73 |
| 2004/0183012 A1 | * | 9/2004 | Yaguchi et al. ................ | 250/311 |
| 2007/0005268 A1 | * | 1/2007 | Higashi .......................... | 702/27 |

OTHER PUBLICATIONS

Zaefferer, Stefan. "New Development of Computer-aided Crystallographic Analysis in Transmission Electron Microscopy" J. Appl. Cryst. (2000). 33, 10-25.*

* cited by examiner

*Primary Examiner* — Brooke Purinton
(74) *Attorney, Agent, or Firm* — J. Clinton Wimbish; Smith Moore Leatherwood LLP

(57) ABSTRACT

Methods of orientation imaging microscopy (OIM) techniques generally performed using transmission electron microscopy (TEM) for nanomaterials using dynamical theory is presented. Methods disclosed may use a wide angle convergent beam electron diffraction for performing OIM by generating a diffraction pattern having at least three diffraction discs that may provide additional information that is not available otherwise.

5 Claims, 7 Drawing Sheets

ORIENTATION IMAGING USING WIDE ANGLE CONVERGENT BEAM DIFFRACTION IN TRANSMISSION ELECTRON MICROSCOPY

RELATED APPLICATIONS

This application is a continuation of U.S. application Ser. No. 13/192,443, filed Jul. 27, 2011, now U.S. Pat. No. 8,748,817, which claims priority to U.S. Provisional Patent Application No. 61/368,154 filed Jul. 27, 2010, the contents of each are incorporated herein by reference in their entireties.

FIELD

This application relates generally to materials imaging, and more specifically to imaging and processing samples to determine grain orientation using transmission electron microscopy (TEM).

BACKGROUND

Grain size statistics, texture, and grain boundary distribution are microstructural characteristics that influence materials properties. These properties include strength, resistivity, and magnetic susceptibility. The microstructural characteristics are usually derived from an orientation map which displays crystallographic orientations of grains in the microstructure. Orientation maps are obtained by performing orientation imaging microscopy (OIM) using a scanning electron microscope (SEM) or a transmission electron microscope (TEM). Orientation imaging microscopy (OIM) using a scanning electron microscope (SEM) is generally performed for materials with grain sizes greater than 60 nm. However, the accuracy of the orientation maps reduces when the grain sizes are less than 60 nm, which is the case with nanomaterials. In these situations, TEMs are used to obtain orientation maps. The OIM techniques are generally performed using a TEM for nanomaterials. These techniques use calculations from the kinematical diffraction theory due to its simplicity. In practice, the electron diffraction in TEM does not necessarily follow a behavior predicted by the kinematical theory.

In literature, four methods have been proposed for performing orientation imaging microscopy (OIM) using TEMs: (1) conical scan method, (2) microbeam spot pattern method, (3) Kikuchi method, and (4) precession method. The first three methods provide correct orientation maps in some cases, however, they have limited applicability for a routine use. Others have applied the conical scan method to a platinum thin film sample but failed to obtain correct orientation maps. (Darbal, A., Barmak, K., Nuhfer, T., Dingley, D. J., Meaden, G., Michael, J., Sun, T., Yao, B., & Coffey, K. R. (2009). Orientation imaging of nanocrystalling platinum films in the TEM. *Microscopy and Microanalysis*, 15, (2), 1232-1233.). Others have discussed drawbacks of the microbeam spot pattern method. (Zaefferer, S. & Wu, G. (2008). Development of a TEM based orientation microscopy system. In *Application of Texture Analysis, Proceedings of International Conference on Texture of Materials*—15, pp. 221-228. New Jersey: Wiley-American Ceramic Society). These have also argued that the Kikuchi method has limited applicability to nanometerials (Wu, G. & Zaefferer, S. (2009) *Ultramicroscopy*, 109, (11), 1317-1325.). Additionally, the Kikuchi method does not accurately determine grain direction in thinner materials because of limitations to the method. Advances in TEM orientation microscopy by combination of dark-field conical scanning and improved image matching. They also attributed the limited applicability to weak intensities of Kikuchi lines due to lattice defects and small grain sizes.

The latest method, known as the precession method, generates spot diffraction patterns in a modified TEM setup requiring additional hardware. The TEM must be modified with the additional proprietary hardware, which is expensive and time consuming to change the TEM back to its unaltered state for other TEM imaging. Subsequently, the precession method applies calculations from the kinemetical diffraction theory to produce orientation maps. This is a relatively new method and a critical evaluation of this method on different material samples is due. However, there are potential problems with this method. First, the physical modifications with additional hardware to the TEM add to the cost of the setup and are often difficult to procure. In addition, authors treated the precession diffraction patterns as the kinemetical diffraction patterns. This treatment may not be correct for certain cases.

SUMMARY

Exemplary automated methods to perform orientation imaging microscopy (OIM) using the dynamical diffraction theory for conventional and scanning TEMs is taught herein. It is known that the dynamical theory is more accurate in describing the electron diffraction in TEMs than the kinemetical theory, but that the complexity of the dynamical theory has thus far prevented others from developing OIM methods and tools using the dynamical method. In addition, the exemplary methods use a wide angle convergent electron beam which provides additional information over narrow-angle convergent electron beams traditionally used in OIM. The wide angle convergent electron beam may be helpful in improving the accuracy of orientation maps. The convergence angle may be selected from an optimized range that with a simulation experiment. Diffraction patterns obtained with wide angle convergent electron beam may be used to calculate crystallographic orientations of grains in the microstructure. Subsequently, these orientations may be used to generate accurate orientation maps.

In some embodiments, a method for orientation imaging microscopy can include obtaining a sample of a material to be imaged, determining an optimized acquisition angle (semi-convergence angle) for a convergence electron beam, applying the convergence electron beam to the sample, wherein convergence beam electron diffraction patterns result in at least three diffraction discs, measuring diffraction patterns of the sample at a plurality of points on said sample using the convergence beam electron diffraction patterns, and processing the diffraction patterns to determine a crystal orientation at each one of the plurality of points on the sample.

In some embodiments the sample has a thickness of about 200 nm or less, or may have a thickness of about 60 nm or less. The orientation imaging microscopy may be performed using one of conventional transmission electron microscopy or scanning transmission electron microscopy. The convergence beam electron diffraction patterns may result in between 6 and 20 diffraction discs with an acquisition angle between about 0 and 50 milliradians. A grain orientation map may also be generated, with the orientation of each grain of the sample is indicated by color.

In some embodiments, method for orientation imaging microscopy may include providing a specimen having a plurality of grains in a plurality of orientations, obtaining information related to the grains of the specimen using transmission electron microscopy, the information including at least three diffraction discs, determining the center of a first diffraction disc of the at least three diffraction discs having the highest diffracted intensity, processing the information related to the grains for the first diffraction disc. Determining the center of a second diffraction disc of the at least three diffraction discs by excluding the information related to the first diffraction disc and locating highest reflected intensity of the remaining diffraction discs, continuing until all diffraction discs are accounted for, and calculating the grain orientations of the plurality of grains of the specimen.

In some embodiments, a method for orientation imaging microscopy may include obtaining a sample of a material to be imaged, applying the convergence electron beam to the sample such that at least three diffraction discs are generated, and collecting dynamical diffraction patterns based on diffraction patterns. Some embodiments may also include processing the dynamical diffraction patterns to determine a crystal orientation at each one of the plurality of points on the sample. The at least three diffraction disks can be non-linearly arranged and may include six or more diffraction discs.

In other methods for orientation imaging microscopy, the method may include obtaining a sample of material to be imaged, applying a convergence electron beam to the sample using transmission electron microscopy to create a diffraction pattern, and processing the diffraction pattern to determine a crystal orientation at each one of a plurality of points on in the diffraction pattern. The processing may include indexing each one of the plurality of points in a diffraction pattern, and comparing the indexed plurality of points with simulated diffraction patterns. The comparing the indexed plurality of points may include improving the accuracy of the crystal orientation based on the comparing.

In some methods of orientation imaging microscopy, the method may include providing a specimen, obtaining a diffraction pattern using transmission electron microscopy, estimating noise in the diffraction pattern, and subtracting the noise from the diffraction pattern to form a corrected diffraction pattern.

BRIEF DESCRIPTION OF THE DRAWINGS

The following description can be better understood in light of Figures, in which:

FIG. 1a is an image matrix obtained according to an exemplary method during extraction of diffraction discs recorded as diffraction pattern $I_{(x,y)}$;

FIG. 1b is an image matrix obtained according to an exemplary method during extraction of diffraction discs recorded as approximated thermal diffusive scattering intensity T;

FIG. 1c is an image matrix of a diffraction pattern obtained according to an exemplary method during extraction of diffraction discs recorded as improved diffraction pattern $D_{x,y}^{(r+1)}$;

FIG. 1d is an image matrix of a diffraction pattern obtained according to an exemplary method during extraction of diffraction discs recorded as binary matrix $B_{(x,y)}$;

FIG. 1e is an image matrix of a diffraction pattern obtained according to an exemplary method during extraction of diffraction discs recorded as diffraction disc $C_{x,y}^{(r)}$;

FIG. 1f is an image matrix of a diffraction pattern obtained according to an exemplary method during extraction of diffraction discs recorded as a modified diffraction pattern $D_{x,y}^{(r+1)}$ at the end of the $r^{th}$ iteration;

Figure 1C:
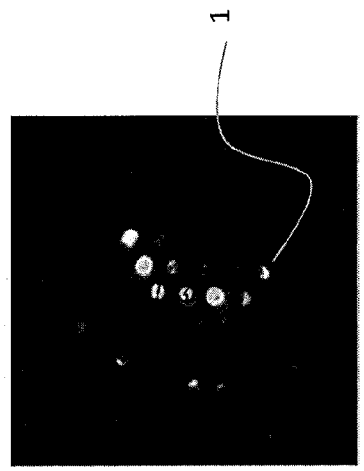
FIGS. 1a-1f are black and white images derived from gray scale images.
Figure 1F:

Together with the following description, the Figures demonstrate and explain the principles of exemplary methods described herein. In the Figures, the size, number and configuration of components may be exaggerated for clarity.

DETAILED DESCRIPTION

The following description supplies specific details in order to provide a thorough understanding. Nevertheless, the skilled artisan would understand that embodiments of imaging using TEM and analysis with dynamic diffraction theory can be implemented and used without employing these specific details. Indeed, exemplary embodiments and associated methods can be placed into practice by modifying the disclosed methods and can be used in conjunction with other devices and techniques conventionally used in the industry.

Embodiments of automated methods to generate orientation maps of a sample material having a thickness up to about 200 nm (or any thickness appropriate for TEM) using TEM and based upon the dynamical theory are taught. The electron diffraction in TEMs is better described by the dynamical theory. Embodiments of OIM methods may use a wide angle convergent beam electron diffraction for collecting material information of a sample to be imaged. The use of the wide angle convergent electron beam provides additional information that is not available otherwise. (Generally, a convergence angle range between about 0 and 25 milliradians may provide the valuable additional information depending on the material of the sample.) Embodiments of OIM methods taught herein exploit the additional information and combines with the calculations from the dynamical theory to provide accurate orientation maps in a conventional or scanning TEM setup. The examples used below were applied to a platinum thin film sample. However, the methods taught herein may be applied to other materials as well.

An interaction of electrons with crystallographic planes in the material sample results in electron diffraction. The crystallographic planes that appear in a diffraction pattern satisfy Bragg's law (2d sin(θ)=nλ) where d is the inter-planar spacing, θ is the diffraction angle, n is the order of diffraction and λ is the wavelength of electrons. The crystallographic planes appear as diffraction discs in a convergent beam electron diffraction pattern obtained using a transmission electron microscope (TEM). The positions of the discs in the diffraction patterns may be utilized to calculate crystallographic orientations of grains in the microstructure.

The crystallographic orientation of a grain may be determined if the diffraction pattern contains at least three non-collinear discs. When the convergence angle (half of an acquisition angle) of the electron beam in TEM is small, the number of the diffraction discs is less and may not be sufficient to calculate crystallographic orientations in some cases. These cases may include two beam condition and systematic row condition of electron diffraction, such as when all discs are collinear. The number of diffraction discs increases with increasing convergence angle. The increase in the number of diffraction discs improves the accuracy of crystallographic orientations required for obtaining orientations maps. However, the diffraction discs tend to overlap at large convergence angles. This overlap has previously been undesired because it can introduce errors in determining the positions of the diffraction discs in the patterns.

The useful information in form of diffraction discs generally increases with convergence angle until the discs start to overlap. Therefore, an optimum range of convergence angles exists for a given sample material that provides at least three non-collinear discs without overlap. Increasing the maximum number of discs without significant overlap increases the accuracy of resulting orientation maps. The optimum range of the convergence angles may be found by analyzing the number for diffraction discs without any disc overlap in simulated diffraction patterns using dynamical diffraction theory. An optimum number of discs to accurately predict grain direction and boundaries may differ based on the sample material used. The number of optimum discs may be at least three and as many as can be accommodated without significant overlap (less than about 20).

Figure 7:
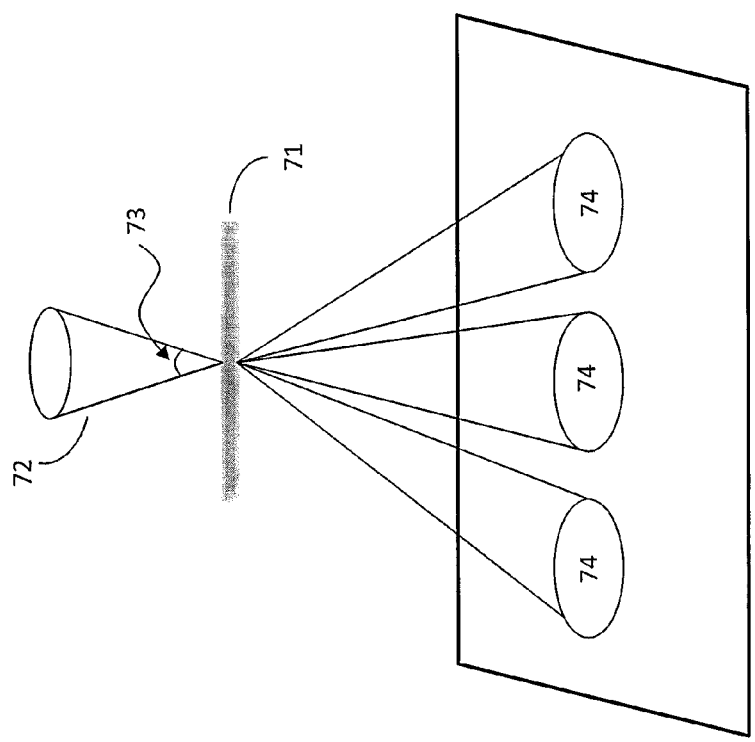
FIG. 7 schematically illustrates applying a convergence electron beam to a sample at an optimized acquisition angle, wherein convergence beam electron diffraction patterns result in at least three diffraction discs.

After selecting a convergence angle from the optimized range, diffraction patterns are obtained using a TEM. FIG. 7 schematically illustrates applying a convergence electron beam (72) to a sample (71) at an optimized acquisition angle (73), wherein convergence beam electron diffraction patterns result in at least three diffraction discs (74). The positions, intensities, and/or sizes of the diffraction discs can be used to index the diffraction patterns. These indexed diffraction patterns can provide crystallographic orientations of the grains in the microstructure. Subsequently, these crystallographic orientations are used to prepare an orientation map. These steps are described below.

The orientation map may be generated from diffraction patterns in three steps: (1) collection of diffraction patterns, (2) disc extraction from the patterns, and (3) orientation mapping. In the first step, a series of diffraction patterns may be collected using the TEM. The positions of the discs from the patterns may be determined in the second step. Similarly, different characteristics, such as position and size may be used in place of intensity to locate each disc and operate in the iterative processes described herein. Finally, the positions of the discs may be used to index the diffraction pattern and obtain the orientation map.

In the first step, diffraction patterns of a material sample may be recorded on a grid of points in the microstructure with a convergence angle chosen from the optimized range. A Digitalmicrograph® script can be used to shift the electron beam and digitally record the diffraction patterns. The microstructure of the sample in a grid of $m_x$ and $m_y$ points may be uniformly divided in two orthogonal directions. A diffraction pattern at each point on the grid may be digitally recorded. Thus, a total of $m_x m_y$ diffraction patterns are obtained in this manner.

A digitally recorded diffraction pattern is a rectangular image with sides of $l_i$ and $l_j$ pixels. We represent a diffraction pattern at location (x,y) on the grid by $I_{(x,y)}$ that is a two dimensional matrix; $x \in [1\ m_x]$, $y \in [1\ m_y]$. The intensity value of a pixel at position (i,j) in the diffraction pattern $I_{(x,y)}$ is represented by $I_{(x,y)}(i,j)$; $i \in [1\ l_i]$, $j \in [1\ l_j]$. Similar notation is used throughout. The value of $I_{(x,y)}(i,j)$ lies in $[0\ (2^b-1)]$ for a diffraction pattern recorded as a b bits image. The lower and the upper limits of $I_{(x,y)}(i,j)$ correspond to a black and a white pixel in the diffraction pattern, respectively. A typical diffraction pattern $I_{(x,y)}$ is shown in FIG. 1a.

To extract the positions of discs in a diffraction pattern, first we obtain improved diffraction pattern $D_{(x,y)}$ by subtracting thermal diffusive intensity T from diffraction pattern $I_{(x,y)}$ as $D_{(x,y)} = I_{(x,y)} - T$. The thermal diffusive intensity (TDS) is a result of atomic vibrations in the sample during collection of diffraction patterns. In practice, TDS is unknown for a diffraction pattern. Thermal diffusive intensity T may be obtained by arithmetic mean of diffraction patterns.

$$T = \frac{1}{m_x m_y} \sum_{x=1}^{m_x} \sum_{y=1}^{m_y} I_{(x,y)}.$$

Figure 1B:
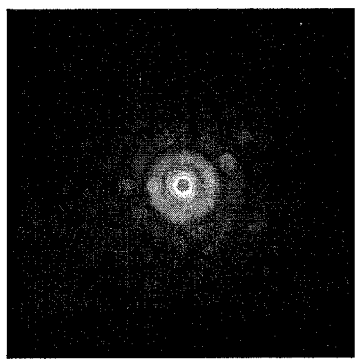
Figure 1E:
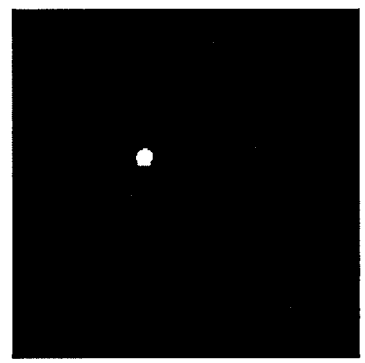
Figure 1A:
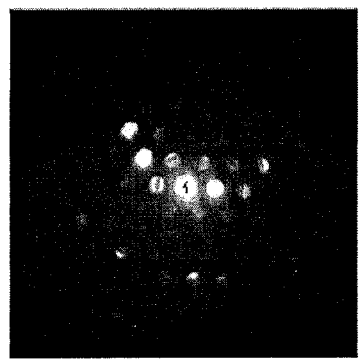
Figure 6A:
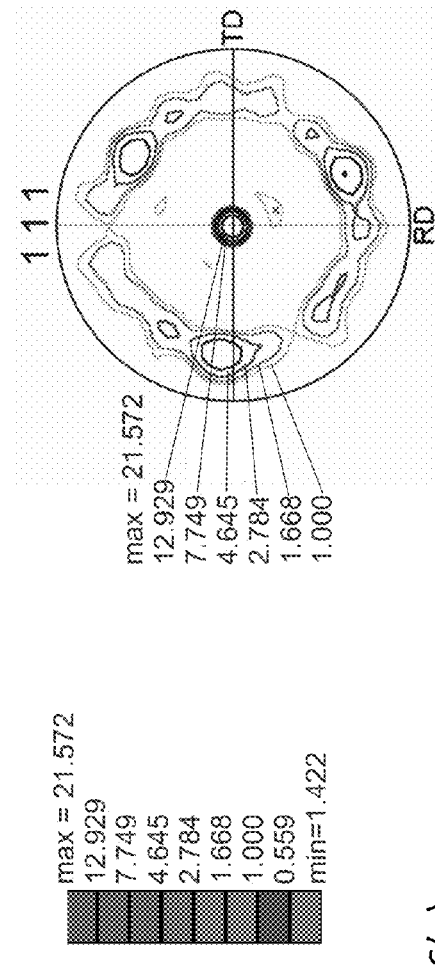
FIGS. 6a-6b are illustrations derived from pole figures illustrating intensity values.
Figure 6B:
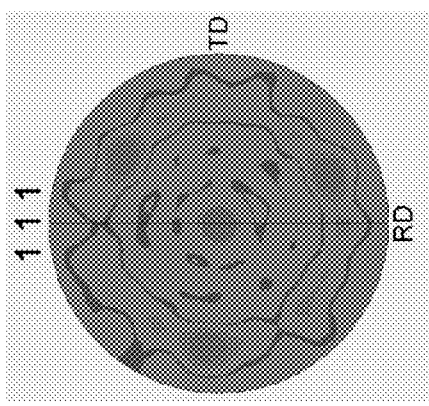
Figure 6C:
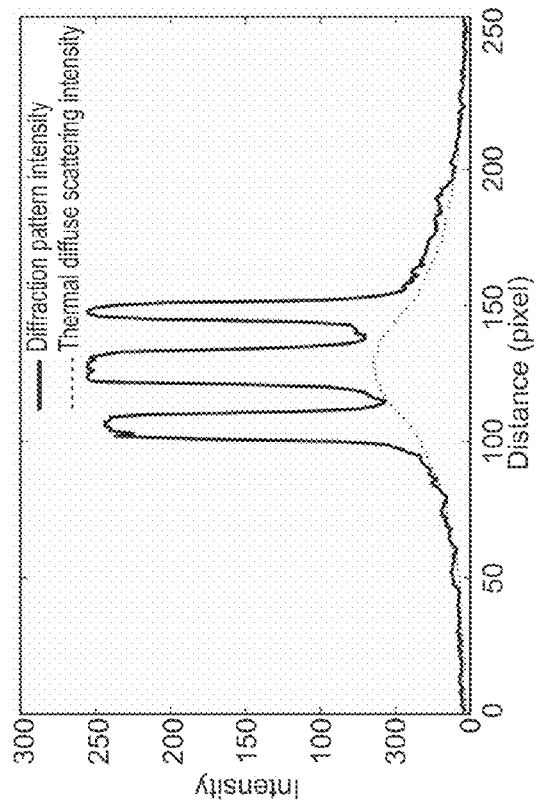
FIG. 6c is a graph of the intensity values of FIG. 1b.

FIGS. 1b and 1c show examples of thermal diffusive intensity T and improved diffraction pattern $D_{(x,y)}$, respectively. As a result of operation in the equation above, discs in FIG. 1c are more distinct than in FIG. 1a. FIG. 6c is a profile of the thermal diffusive intensity of FIG. 1b. The improved diffraction pattern $D_{(x,y)}$ contains contiguous regions that are relatively brighter than their neighboring regions as exhibited by disc (1) of FIG. 1c. These regions are known as diffraction discs. The diffraction pattern $D_{(x,y)}$ contains discs of different intensities.

For example, FIG. 1c shows that discs closer to the center of the diffraction pattern have higher intensities and vice versa. Locations of these discs within a diffraction pattern need to be known as the first step for creating an orientation map. These discs can be extracted using 'edge finding algorithms' popular in image processing. However, if these methods are applied to obtain positions of all of the discs simultaneously, discs with relatively low intensities may not be detected. The low intensity discs contain important information regarding crystallographic orientations of grains as well. Alternatively, positions of the discs may be obtained one by one using a procedure applied in $N_r$ iterations. In each iteration, position of one the diffraction discs may be obtained using a three step procedure.

In the following description, the three step procedure is described for the (i,j) pixel in the diffraction pattern recorded at (x,y) location in the microstructure. The same processing is applied to all the pixels (i,j) for that diffraction pattern; $\in [1\ l_i]$, $i \in [1\ l_j]$, j. In the $r^{th}$ iteration (r=1 ... $N_r$), diffraction intensity matrix $D_{(x,y)}^{(r)}$ may be used to roughly estimate the position of the $r^{th}$ diffraction disc. Next, the position of the $r^{th}$ diffraction disc is accurately determined. Finally, the intensity values of pixels of $r^{th}$ disc are set to zero. This change in intensities may avoid the interference due to $r^{th}$ disc in obtaining the positions of other discs. The selection of the $r^{th}$ disc can be made based on maximum intensity, integrated intensity, size, etc. These three steps are described below.

Figure 1D:

To begin the iterative process, $D_{(x,y)}^{(1)}$ is obtained from the improved diffraction pattern $D_{(x,y)}$ by contrast expansion as $$D_{(x,y)}^{(1)}(i,j) = (2^b - 1)\frac{D_{(x,y)}(i,j) - \text{MIN}(D_{(x,y)})}{\text{MAX}(D_{(x,y)})}$$

where MIN(A) and MAX(A) represent the minimal and maximal element of matrix A, respectively. Now, for the rough estimation of the $r^{th}$ disc, a thresholding operation is applied to obtain a binary matrix $B_{(x,y)}^{(r)}$.

$$B_{(x,y)}^{(r)}(i,j) = \begin{cases} 1 & \text{if } D_{(x,y)}^{(r)}(i,j) > t_h \\ 0 & \text{if } D_{(x,y)}^{(r)}(i,j) \leq t_h \end{cases}$$

where threshold $t_h$ is a positive integer such that $t_h<(2^b-1)$. FIG. 1(d) shows a typical binary matrix $B_{(x,y)}^{(r)}$ after the thresholding operation. The matrix $B_{(x,y)}^{(r)}$ contains contiguous regions of nonzero valued elements. Each of the contiguous regions of nonzero elements roughly corresponds to one of the diffraction discs in the pattern. These regions can be separated by the 8-connected component analysis. The 8-connected component analysis can separate the regions based upon the intensity value of a pixel and its 8 neighbors. The contiguous region $C_{(x,y)}^{(r)}$ is obtained of the highest intensity in $B_{(x,y)}^{(r)}$ using the 8-connected component analysis. Regions may also be obtained through maximum intensity, maximum size, etc. This contiguous region can roughly correspond to the $r^{th}$ diffraction disc. Once the region of the $r^{th}$ disc is roughly known, the position of the disc can be roughly indicated by $(P_{(x,y),i}^{(r)}, P_{(x,y),j}^{(r)})$ as $$(P_{(x,y),i}^{(r)}, P_{(x,y),j}^{(r)}) = \left( \frac{\sum_{i=1}^{l_i}\sum_{j=1}^{l_j} i C_{(x,y)}^{(r)}(i,j) D_{(x,y)}^{(r)}(i,j)}{\sum_{i=1}^{l_x}\sum_{j=1}^{l_j} C_{(x,y)}^{(r)}(i,j)}, \frac{\sum_{i=1}^{l_i}\sum_{j=1}^{l_j} j C_{(x,y)}^{(r)}(i,j) D_{(x,y)}^{(r)}(i,j)}{\sum_{i=1}^{l_x}\sum_{j=1}^{l_j} C_{(x,y)}^{(r)}(i,j)} \right)$$

Next, the position of the $r^{th}$ disc may be accurately determined using the roughly estimated position $(P_{(x,y),i}^{(r)}, P_{(x,y),j}^{(r)})$. The accurate determination may begin with a thresholding operation to obtain binary matrix $B'_{(x,y)}^{(r)}$.

$$B'_{(x,y)}^{(r)}(i,j) = \begin{cases} 1 & \text{if } D_{(x,y)}(i,j) > t_l \ \& \ |i - P_{(x,y),i}^{(r)}| < d_c \ \& \ |j - P_{(x,y),j}^{(r)}| < d_c \\ 0 & \text{otherwise} \end{cases}$$

where, threshold ti is a positive integer such that $t_l<t_h$, $d_c$ is the diameter of the diffraction disc formed by direct electron beam, and |A| refers to the magnitude of A. The value of $d_c$ depends upon the convergence angle and the camera constant $l_c$ used during the collection of diffraction patterns. $B'_{(x,y)}^{(r)}$ contains contiguous regions of nonzero valued elements. Similar to the rough estimation described before, the 8-connected component analysis may be applied on $B'_{(x,y)}^{(r)}$ to obtain the contiguous region $C'_{(x,y)}^{(r)}$ corresponding to the disc of the highest intensity in $D_{(x,y)}^{(r)}$, or may correspond to other parameters such as integral intensity, size, etc. The accurate position $(P_{(x,y),i}^{(r)}, P_{(x,y),j}^{(r)})$ of the $r^{th}$ diffraction disc may be determined using $C'_{(x,y)}^{(r)}$ as above.

Subsequently, the intensities of pixels of the $r^{th}$ disc are set to zero in $D_{(x,y)}^{(r)}$ for extraction of the $(r+1)^{th}$ disc as $D'_{(x,y)}^{(r)}(i,j) = D_{x,y}^{(r)}(i,j)[1 - C'_{(x,y)}^{(r)}(i,j)]$.

Finally, the contrast expansion operation may be performed on $D'_{(x,y)}^{(r)}$ to obtain $D_{(x,y)}^{(r+1)}$ needed for extraction of $(r+1)^{th}$ diffraction disc.

$$D_{(x,y)}^{(r+1)}(i,j) = (2^b - 1)\frac{D'_{(x,y)}^{(r)}(i,j) - \text{MIN}(D'_{(x,y)}^{(r)})}{\text{MAX}(D'_{(x,y)}^{(r)})}.$$

Figure 2A:
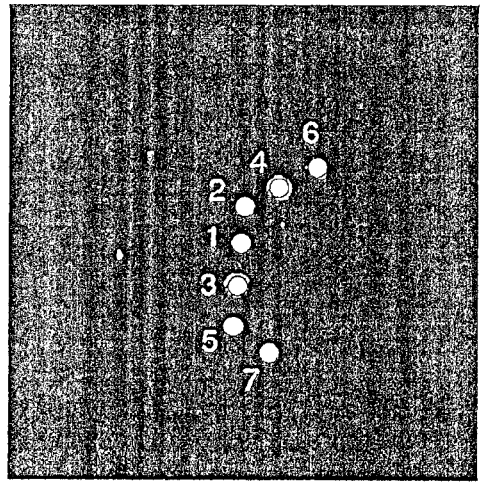
FIG. 2a is an image matrix of a diffraction pattern obtained according to an exemplary method during indexing of diffraction discs including indicated positions of diffraction discs.

The above described procedure may be iteratively repeated $N_r$ times. These iterations may provide the positions of $N_r$ diffraction discs which are used to generate the orientation map for the sample under test. As an example, FIG. 2a displays the positions of diffraction discs in the diffraction pattern.

An orientation map may display crystallographic orientations of grains obtained by indexing the diffraction patterns $I_{(x,y)}$; $x \in [1\ m_x]$, $y \in [1\ m_y]$. The indexing of a diffraction pattern involves assignment of crystallographic planes or reciprocal lattice points to diffraction discs found in the previous step. We apply the dynamical diffraction theory in indexing of the pattern. This application resulted in inclusion of forbidden crystallographic planes with zero structure factors. In addition, we include higher order Laue zone planes that increase the accuracy of the crystallographic orientations especially in the cases of 180° ambiguity. We represent the position vector of a reciprocal lattice point by g.

The assignment of the reciprocal lattice points to individual discs is referred to as a solution of the diffraction pattern herein. The correct solution contains reciprocal lattice points that were diffracting during the collection of the diffraction pattern. The correct solution may be found using indexing procedure which is performed by comparing distances and angles between diffraction discs with distances and angles between assigned reciprocal lattice points. If more than one solution exists for a diffraction pattern from the distance and angle comparison, the correct solution may be found by a comparison with the simulated diffraction patterns. The steps for indexing the diffraction patterns and creating the orientation map are described below.

First, the reciprocal lattice points may be assigned to individual discs in the diffraction pattern. This step begins with identification of disc formed by the direct electron beam. This disc, referred to as the central diffraction disc, is generally located at $(l_i/2, l_j/2)$ in the diffraction pattern. Let $(P_{(x,y),i}^{(c)}, P_{(x,y),j}^{(c)})$ be the position of the central disc. The reciprocal lattice point (0 0 0) may be assigned to the central diffraction disc. The rest of the assignments may be based upon the length of g vectors and the distance between individual discs and the central diffraction disc. Matrices $E_{x,y}^{(r)}$ ($r=1 \ldots N_r$) may be produced that contain reciprocal lattice points associated with diffraction discs as $$E_{(x,y)}^{(r)} = \left\{ \{g\} : \left| \sqrt{(P_{(x,y),i}^{(r)} - P_{(x,y),i}^{(c)})^2 + (P_{(x,y),j}^{(r)} - P_{(x,y),j}^{(c)})^2} - \frac{\|g\|}{l_c} \right| < t_d \right\}$$

where $\|A\|$ refers to length of a vector A and $t_d$ is distance tolerance such that $t_d < d_c$.

Next, matrices $E_{(x,y)}^{(r)}$ may be used to determine the correct solution of the diffraction pattern by comparing angles between discs and angles between assigned reciprocal lattice points. The angle comparison begins with finding all of the possible solutions of the diffraction pattern from $E_{(x,y)}^{(r)}$. If $E_{(x,y)}^{(r)}(s)$ is the $s^{th}$ element of matrix, a solution $U_{(x,y)}^{(f)}$ of the diffraction pattern can be written as $$U_{(x,y)}^f = [E_{(x,y)}^{(1)}(s_1) E_{(x,y)}^{(2)}(s_2) E_{(x,y)}^{(3)}(s_3) \ldots E_{(x,y)}^{(N_r)}(s_{N_r})]$$

where $s_p \in [1 \ \overline{E_{(x,y)}^p}]$ and $\overline{A}$ is the number of elements in matrix A. The total number F of possible solutions as the one described in the equation above is given by $$F = \prod_{r=1}^{N_r} \overline{E_{(x,y)}^{(r)}}.$$

Angles between the discs and angles between reciprocal lattice points may be compared to find the correct solution in $U_{(x,y)}^f$; $f \in [1 \ F]$. Angle $q_{(x,y)}^{(r)}$ may be used for the comparison $$q_{(x,y)}^{(r)} = \left| \left( \frac{P_{(x,y),j}^{(r)} - P_{(x,y),j}^{(c)}}{P_{(x,y),i}^{(r)} - P_{(x,y),i}^{(c)}} - \frac{P_{(x,y),j}^{(r+1)} - P_{(x,y),j}^{(c)}}{P_{(x,y),i}^{(r+1)} - P_{(x,y),i}^{(c)}} \right) - L(g_{(x,y)}^{(r+1)}, g_{(x,y)}^{(r)}) \right|$$

where $g_{(x,y)}^{(r)}$ is the position vector of reciprocal lattice point assigned to the $r^{th}$ disc in the solution $U_{(x,y)}^f$ and $r \in [1(N_r-1)]$. The solution $U_{(x,y)}^f$ is considered the correct solution if $q_{(x,y)}^{(r)} \leq t_q$ for all $r \in [1(N_r-1)]$ & $r \neq c$.

Figure 2B:
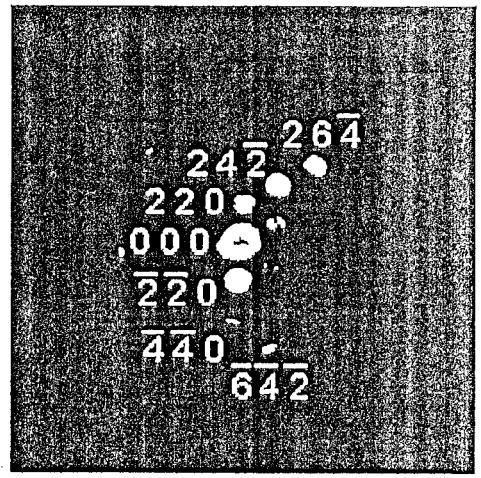
FIG. 2b is an image matrix of a diffraction pattern obtained according to an exemplary method during indexing of diffraction discs including a correctly indexed diffraction pattern.
Figure 2C:
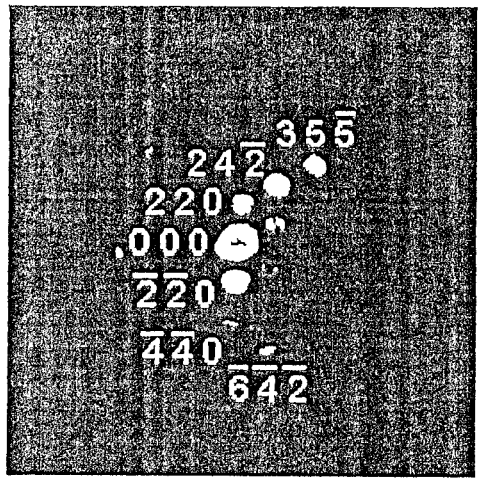
FIG. 2c is an image matrix of a diffraction pattern obtained according to an exemplary method during indexing of diffraction discs including an incorrectly indexed diffraction pattern.
Figure 2D:
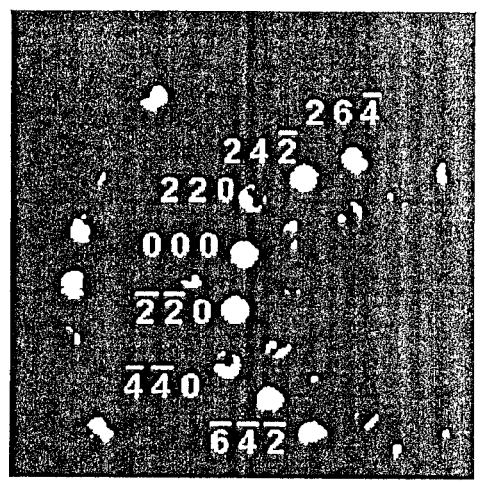
FIG. 2d is an image matrix of a diffraction pattern obtained according to an exemplary method during indexing of diffraction discs including a correctly indexed diffraction pattern and a corresponding simulated diffraction pattern.

All of the F solutions may be tested using angle comparison given by the equation above to separate incorrect solutions. We form a set $V_{(x,y)}$ which contains solutions satisfying the angle comparison test. FIGS. 2b and 2c show two solutions in a typical set $I_{(x,y)}$. Subsequently, the correct solution in $V_{(x,y)}$ may be found by a comparison between elements of $V_{(x,y)}$ and simulated diffraction patterns. For comparison, diffraction patterns covering all possible crystallographic orientations were simulated using existing Bloch wave approaches. The comparison may be performed using a computer by considering reciprocal lattice points in the solutions and in the simulated patterns. A solution in $V_{(x,y)}$ containing the maximum number of reciprocal lattice points which are also present in any of the simulated diffraction patterns may be considered as the correct solution. FIG. 2d shows the best match after comparison of solutions in $V_{(x,y)}$ with simulated diffraction patterns. The comparison also provided the zone axis $[h_{(x,y)} k_{(x,y)} l_{(x,y)}]$ of the diffraction pattern $I_{(x,y)}$ which will be used in calculation of crystallographic orientation.

It is possible that the comparison described above results in multiple solutions with equal probabilities. These solutions may indicate an ambiguity in the indexing procedure. This ambiguity can be alleviated by performing indexing with a larger value of number of discs $N_r$. If ambiguities still persist, the microscopy may be performed again with a smaller camera length to obtain sufficient number of diffraction discs in the patterns.

Finally, the crystallographic orientation of the grain may be determined from the correct solution obtained above in terms of three Euler angles ($\phi$, $\Phi$, $\phi_2$). The Euler angles ($\phi_1(x,y)$, $\Phi(x,y)$, $\phi_2(x,y)$) of the diffraction pattern $I_{(x,y)}$ can be obtained using zone axis $[h_{(x,y)} k_{(x,y)} l_{(x,y)}]$ and one of the diffraction discs. Let $(h_r, k_r, l_r)$ be the reciprocal lattice point assigned to the $r^{th}$ diffraction disc in the correct solution; $r \neq c$. The crystallographic orientation which is independent of choice of r can be given as $$\phi_1(x,y) = \sin^{-1}\left( \frac{\sqrt{h_{(x,y)}^2 + k_{(x,y)}^2}}{\sqrt{h_{(x,y)}^2 + k_{(x,y)}^2 + l_{(x,y)}^2}} \frac{l_r}{\sqrt{h_r^2 + k_r^2 + l_r^2}} \right) - a\tan 2\left( \frac{P_{(x,y),j}^{(r)} - P_{(x,y),j}^{(c)}}{P_{(x,y),i}^{(r)} - P_{(x,y),i}^{(c)}} \right)$$

$$\Phi(x,y) = \cos^{-1}\left( \frac{l_{(x,y)}}{\sqrt{h_{(x,y)}^2 + k_{(x,y)}^2 + l_{(x,y)}^2}} \right)$$

$$\phi_2(x,y) = \tan^{-1}\left( \frac{k_{(x,y)}}{h_{(x,y)}} \right)$$

where a tan 2 is the two argument arc tangent function. The Euler angles for the diffraction patterns at all of the points (x,y) in the microstructure are calculated. The Euler angles and positions (x,y) of the diffraction patterns are subsequently used to produce the orientation map.

The sample axes system for crystallographic orientation described above has x and z axis parallel to sample holder and optical axis in the TEM, respectively. However, any axis convention may be used as desired. The third axis is perpendicular to x and z axes. It is sometimes possible to have an angle difference between image mode and diffraction mode of TEM. This difference alters the value of $\phi_1$ calculated above. An $\alpha$-MoO$_3$ crystal can be used to calculate this angle and subsequently modify the value of $\phi_1$.

In addition to any previously indicated modification, numerous other variations and alternative arrangements can be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use can be made without departing from the principles and concepts set forth herein. Also, as used herein, examples are meant to be illustrative only and should not be construed to be limiting in any manner.

Example 1

Methods described herein may be performed with a variety of materials and different tools. The method used to produce the images of the figures was applied to perform orientation imaging microscopy on a platinum thin film sample. The thin film sample was prepared by sputter depositing a 35 nm platinum layer on an oxidized silicon wafer. The thin film sample was annealed at 800° C. for 1 min to avoid superimposing grains. A TEM sample from this thin film sample was prepared.

Figure 3:
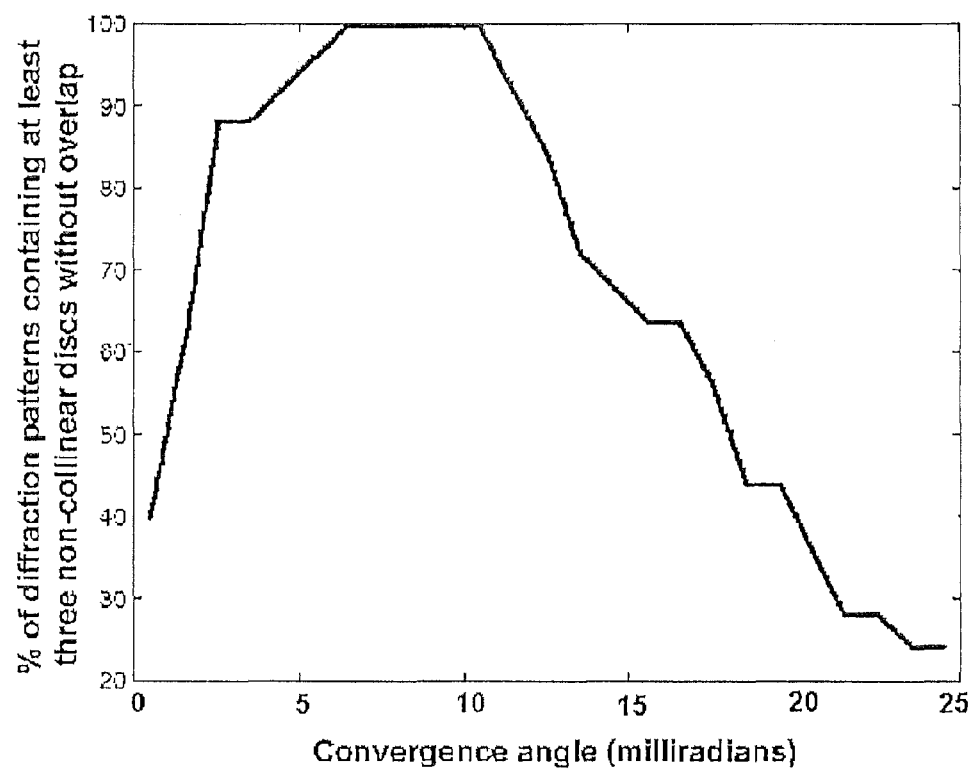
FIG. 3 is a graph of a convergence angle optimization determination.

In order to apply an exemplary method on the platinum TEM sample, the convergence angle was first optimized according to the simulation experiment described above. Diffraction patterns of 50 randomly oriented grains were simulated with various convergence angles using the Bloch wave approach of dynamical diffraction theory. FIG. 3 shows the percentage of diffraction patterns that contained at least three non-collinear discs without overlap. The optimized range of the convergence angle (or half of the acquisition angle) was found to be between 1 to 25 milliradian, or better between about 6 and 10.5 milliradians because in this range all of the diffraction patterns contained the required discs.

Figure 4B:
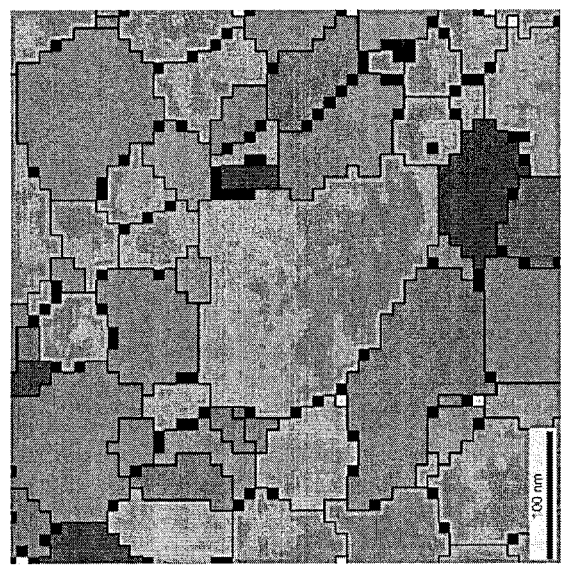
FIG. 4b is an illustration derived from a grain map produced according to exemplary methods.
Figure 4A:
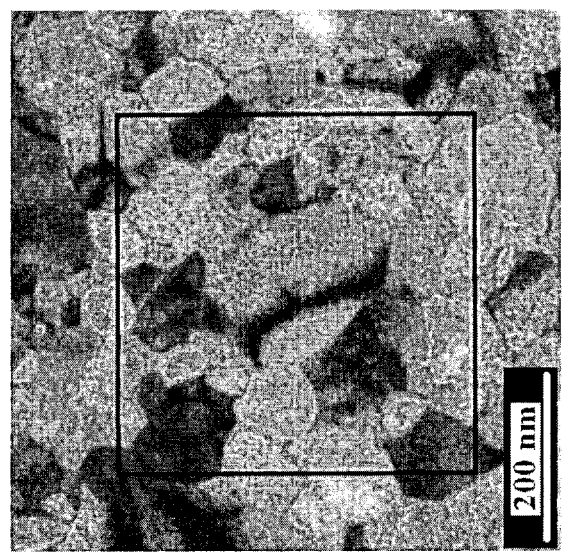
FIG. 4a is an illustration derived from a bright field micrograph.
Figure 5A:
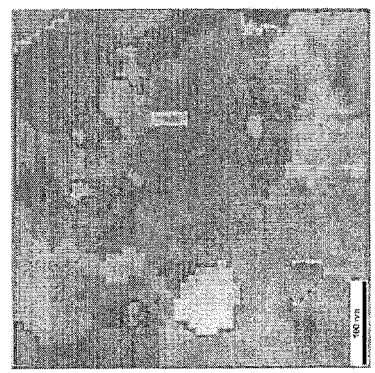
FIGS. 5a-5c are illustrations derived from inverse pole figure maps produced according to exemplary methods.
Figure 5B:
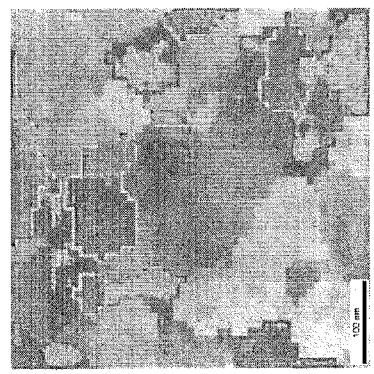
Figure 5C:
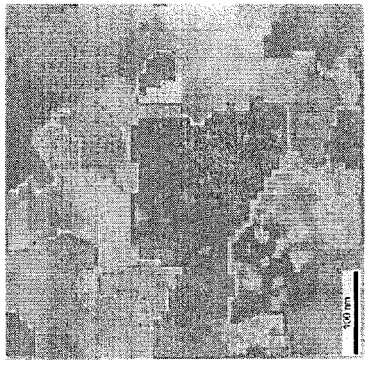
Figure 5D:
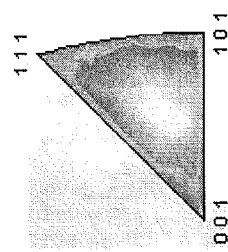
FIG. 5d is an illustration of a scale of orientation for the maps of FIGS. 5a-5c.
Figure 5E:
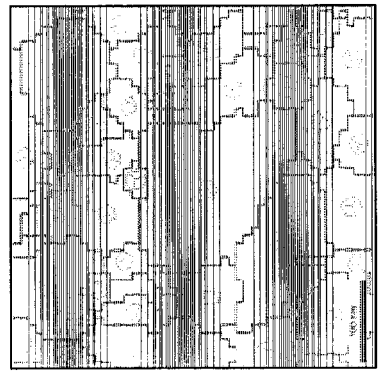
FIG. 5e is a illustration derived from an orientation map.

The diffraction patterns were recorded in a TECHNAI® F30 transmission electron microscope at 300 kV accelerating voltage, 12 spot size and 5.5 milliradians convergence angle. The convergence angle of 5.5 milliradians was the best available choice in the TEM near the desired range of 6 to 10.5 milliradians. The illustration of a bright field micrograph in FIG. 4(a) shows the microstructure of the sample. The diffraction patterns were recorded on a square grid of 50×50 points with 9 nm spacing in the microstructure. An exposure of 1 second was used in a ccd camera for recording the patterns. The outline of the square grid can be seen in FIG. 4(a).

Although this area may be small for a reliable statistics of texture information, it is suitable for demonstrating the application of exemplary methods. The positions of discs in the diffraction patterns were obtained using disc extraction technique described above. The choice of parameters during disc extraction of discs was: $t_h=80$, $t_l=20$, and $d_c=14$ pixels. The parameters used for indexing the diffraction patterns and obtaining the orientation map of FIG. 4 were chosen as: $l_c=0.32462$ nm$^{-1}$ per pixel, $t_d=1.7$ nm$^{-1}$ and $t_q=10°$. A set of 90×90×90 uniformly distributed diffraction patterns in $0 \leq \phi_1 < 90°$, $0 \leq \cos^{-1} < 1$, $0 \leq \phi_2 < 90°$ were simulated using 05.5 milliradians convergence angle, 300 kV potential and 35 nm thick platinum sample for obtaining orientations as described above.

The crystallographic orientations obtained with parameters described above were used to produce a grain map. Grain maps may display grains in the microstructure using unique colors. FIG. 4b is an approximation of a color grain map. It can be observed from FIG. 4b that the grain structure in the grain map is similar to the grain structure in simulated the bright field micrograph of FIG. 4a because shapes of the grains in both of the Figures are similar. A heart shaped grain can be noticed in the center of the grain map and the bright field micrograph. In FIG. 4b, a few pixels belong to incorrectly indexed diffraction patterns and may be indicated in black or other contrasting color on a color grain map. It should be noted that most of these pixels lie on grain boundaries and comprise of less than 5% of the grain map area. These pixels may be a result of overlapping diffraction patterns obtained at the grain boundaries.

The crystallographic orientations obtained using the method of this paper were used to generate orientation maps of platinum thin film sample which are shown approximately in FIG. 5 inverse pole figure (IPF) maps. IPF maps may be produced in color to provide additional information such as intensity. These maps are cleaned using neighbor orientation correlation (level 3) scheme describe in *Metallurgical and Materials Transactions* A, vol. 37, No. 3, pp. 599-607 to discard incorrectly indexed diffraction patterns. An orientation of crystallographic directions in a grain with respect to directions in the platinum thin film sample can be inferred from IPF maps. FIG. 5a shows the IPF map projected parallel to the thin film normal. The IPF maps may be and would generally be produced in color. For example, a predominance of blue color may indicate a strong <1 1 1>|| surface normal texture. FIGS. 5b and 5c show IPF maps projected along two orthogonal directions in plane of the thin film sample. IPF maps in FIGS. 5b and 5c do not represent a strong color preference which would indicate that there is no strongly preferred orientation along the <1 1 1> texture peak. This strong preference of <1 1 1>|| surface normal texture and absence of preference in plane of the film indicates that the platinum thin film sample contain a <1 1 1>|| surface normal fiber texture. FIG. 5e illustrates orientations in an alternative form.

Pole figures showing positions of crystallographic plane normals relative to the reference sample axes as projections, can be used to describe the orientation preference of the grains. FIGS. 6a and 6b shows the {1 1 1} pole figure prepared from crystallographic orientations obtained using method of this paper. The {1 1 1} pole figure contains a high intensity peak at the center and a moderate intensity ring around it. The high intensity peak in the center indicates that most of the grains in the sample are oriented such that the {1 1 1} crystallographic plane normals are parallel to the sample normal. A continuous ring of moderate intensity indicates that the grains have no orientation preference in the plane of thin film. This orientation preference in pole figure confirms the presence of <1 1 1>|| surface normal fiber texture in the platinum sample.

Most thin films samples prepared by sputter deposition are known to have strong texture preference. It has been reported that the platinum thin films, such as used in this paper contain <1 1 1>|| surface normal fiber texture. Therefore, results obtained from the method as performed for this example are in good agreement with known texture analysis.

The invention claimed is:

1. A method for orientation imaging microscopy, the method comprising:
   providing a specimen having a plurality of grains in a plurality of orientations;
   obtaining information related to the grains of the specimen using transmission electron microscopy, the information including at least three diffraction discs;
   determining the center of a first diffraction disc of the at least three diffraction discs;
   processing the information related to the grains for the first diffraction disc;
   determining the center of a second diffraction disc of the at least three diffraction discs by excluding the information related to the first diffraction disc; and
   calculating the grain orientations of the plurality of grains of the specimen.

2. The method of claim 1, wherein the first diffraction disc is selected based on one of intensity, location, or size of each of the at least three diffraction discs.

3. The method of claim 1, wherein the specimen has a thickness 60 nm or less.

4. The method of claim 1, wherein the orientation imaging microscopy is performed using one conventional transmission electron microscopy or scanning transmission electron microscopy.

5. The method of claim 1, wherein the information includes between 6 and 20 diffraction discs.

* * * * *